(12) United States Patent
Magnusson

(10) Patent No.: US 6,390,095 B1
(45) Date of Patent: May 21, 2002

(54) PENILE ERECTION COLLAR

(76) Inventor: Jan Magnusson, 117 Wild Wood Beach Rd., Mahtomedi, MN (US) 55115

( * ) Notice: Subject to any disclaimer, the term of this patent is extended or adjusted under 35 U.S.C. 154(b) by 0 days.

(21) Appl. No.: 09/712,507

(22) Filed: Nov. 14, 2000

(51) Int. Cl.$^7$ .................................................. A61F 6/02
(52) U.S. Cl. ........................................ 128/842; 600/39
(58) Field of Search .................................. 128/842, 844, 128/918; 600/37, 38, 39

(56) References Cited

U.S. PATENT DOCUMENTS

| | | | | |
|---|---|---|---|---|
| 4,203,432 A | * | 5/1980 | Koch | 128/79 |
| 4,960,113 A | * | 10/1990 | Seeberg-Elverfeldt | 128/79 |
| 4,995,381 A | * | 2/1991 | Marmar | 128/79 |
| 5,246,015 A | * | 9/1993 | Baber | 600/39 |

* cited by examiner

Primary Examiner—Michael A. Brown
(74) Attorney, Agent, or Firm—D L Tschida

(57) ABSTRACT

A penile constriction collar that provides a relatively constant constriction pressure to a penis between flaccid and tumescent conditions. The collar is molded from medical grade silicone rubber having a durometer of 40–50 (±5) on the Shore "A" scale and exhibits a constriction force of 1.5 Kg (±0.5 Kg) over a range of changing diameter equal to or greater than 150%. One preferred collar exhibits a torroid or O'ring shape. Collars constructed with multiple regions of differing durometer and/or selected cross section shapes, and color can also be constructed to assure user comfort in erect and flaccid states.

22 Claims, 3 Drawing Sheets

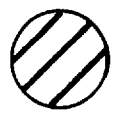
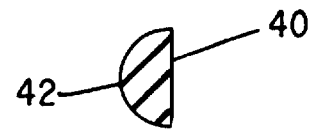
FIG. 3         FIG. 5
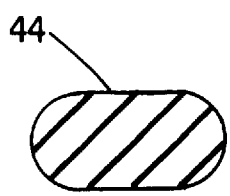
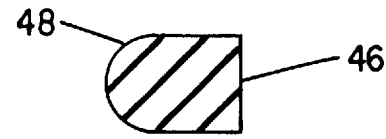
FIG. 6         FIG. 7

PENILE ERECTION COLLAR

BACKGROUND OF THE INVENTION

The present invention relates to male therapeutic devices and, in particular, to a constriction collar for facilitating and sustaining an erection.

In order to achieve an erection, blood flow into the penis via the cavernosal arteries must increase and venous outflow must be drastically reduced or stopped altogether. During sexual stimulation, neurotransmitters are released that relax smooth muscle in the penile arterial system (i.e. cavernosal arteries) and the penile tissue (i.e. paired cavernosal bodies and sinusoids). Smooth muscle relaxation in the arterial system results in vasodilatation with increased blood flow into the penis with accompanying penile tumescence or swelling. Smooth muscle relaxation in the penile tissue results in relaxation of the sinusoidal spaces that engorge with blood and physically occlude the penile veins as they exit the tunical albuginea (i.e. firm layer that encloses the penile tissue and blood vessels).

Failure to occlude sufficiently the penile veins leads to poor entrapment of blood within the penile erectile bodies, commonly referred to as venous leakage. Venous leakage causes poor maintenance of erections and is a major cause of erectile dysfunction.

Presently known, fixed diameter constriction collars or rings provide a relatively small diameter to assure retention to the penis in a flaccid condition. During penile tumescence, the collar expands to place an increased tension on the penis to achieve venous occlusion. Most typically, too much tension results and the constriction collar becomes too tight and creates discomfiture. Undue tension or compression for protracted periods of time also heightens the risk of tissue damage, even though an erection is maintained.

The hardness, or durometer, of the material used to construct the collar is also a significant factor. If the material is too soft, an erection from the flaccid state may not be easily achieved. If the material is too hard and/or too much tension is placed on the penis, tissue damage may occur. As a result, the durometer of the material is critical to the function, as well as comfort, of a constriction ring.

U.S. Pat. Nos. 4,203,432; 4,224,933 and 5,085,209 disclose adjustable, discontinuous circumference constriction devices. That is, the user controls the effective device diameter to vary the constriction force exhibited by the device.

U.S. Pat. Nos. 5,246,015 and 5,628,329 disclose closed loop or continuous circumference collars of tubular or cylindrical construction. Each provides gripping flanges that facilitate mounting and removal.

In distinction to known penile restriction devices, the present collar was developed to provide a constant and comfortable compressive force or tension (i.e. 1.5 Kg (±0.5 Kg)) measured as a quasi-static load) over a wide range of flaccid and tumescent penile diameters. The collar is constructed of a medical grade silicone material that is rated between 40–50 durometer (±5) on the Shore "A" scale. The material is firm enough to cause and sustain an erection. Collars constructed with multiple regions of differing relative durometer and/or cross section shape have also been considered.

The collar provides a non-pharmacological penile constriction device that enhances venous occlusion and improves the ability to trap blood within the penis over a range of penile diameters. The collar enhances patient comfort, decreases the potential for tissue injury and enhances erectile performance (i.e. the ability for a man to achieve and maintain an erection sufficient for satisfactory sexual intercourse), sexual function, and sexual partner satisfaction.

SUMMARY OF THE INVENTION

It is accordingly a primary object of the invention to provide an elastomer penile constriction collar.

It is a further object of the invention to provide a constriction collar formed from a medical grade silicone rubber exhibiting a durometer in the range of 40–50 (±5) on the Shore "A" scale.

It is a further object of the invention to provide a collar that exhibits a constriction load of 1.5 Kg (±0.5 Kg) over a range of increasing diameter equal to or greater than 150%.

It is a further object of the invention to provide a torroid shaped constriction collar.

It is a further object of the invention to provide a constriction collar having multiple circumferential regions or zones that exhibit differing durometers and/or cross sectional shapes.

Many of the foregoing objects, advantages and distinctions of the invention are obtained in a number of alternative collars. The collar is designed to provide a relatively constant compressive force over a range of changing penile diameters and tumescence to maintain comfort from the non-erect or flaccid state to the erect condition. The compressive force provides sufficient compression to cause an erection and to occlude blood flow sufficiently to achieve and maintain an erection satisfactory for sexual intercourse. Some men also believe penile engorgement enhances the penile sensation experienced during intercourse.

Still other objects, advantages, distinctions and alternative constructions and/or combinations of the invention will become more apparent from the following description with respect to the appended drawings. Similar components and assemblies are referred to in the various drawings with similar alphanumeric reference characters. The description should not be literally construed in limitation of the invention. Rather, the invention should be interpreted within the broad scope of the further appended claims.

DESCRIPTION OF THE DRAWINGS

FIG. 3 shows a circular cross section view through the collar of FIG. 2.

FIG. 5 shows a flat inner surface and semi-circular outer cross-section shape that might be exhibited at one or more regions of a multi-region collar such as shown in FIG. 4.

FIG. 6 shows an elliptical cross-section shape having that might be exhibited at one or more regions of a multi-region collar such as shown in FIG. 4.

FIG. 7 shows a flat inner surface and an elliptical or ovular outer cross-section shape that might be exhibited at one or more regions of a multi-region collar such as shown in FIG. 4.

Similar structure at the drawings is referred to with the same reference numerals and/or characters.

DESCRIPTION OF THE PREFERRED EMBODIMENT

Figure 1:
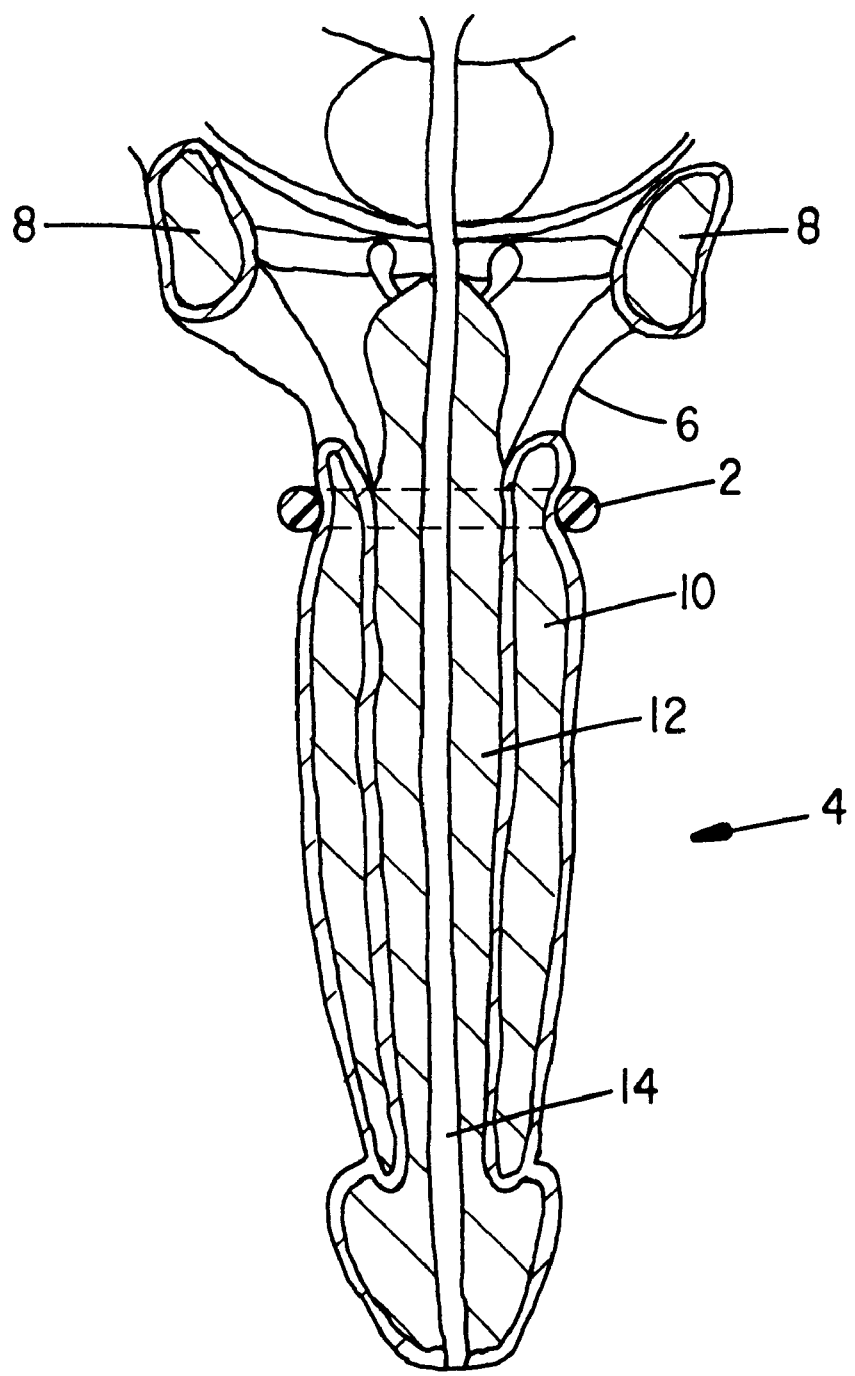
FIG. 1 shows a cross section view of a penis fitted with the constriction collar of the invention.

Referring to FIG. 1, a view is shown to an elastomer constriction collar 2 of the invention mounted to a penis 4. The collar 2 is typically mounted to the base of the penis 4 adjacent the abdomen and above the scrotum 6 and testes 8. The collar 2 principally constricts the corpus cavernosum tissue 10 and which contains the paired cavernosal bodies and sinusoids. The corpus spongiosum 12 and urethra 14 experience lesser constriction, due to their position within the penis and such that ejaculation is not precluded. The collar 2 is normally mounted to the penis 4, while flaccid or before erection, to facilitate a comfortable fit, although it can be mounted after.

Figure 2:
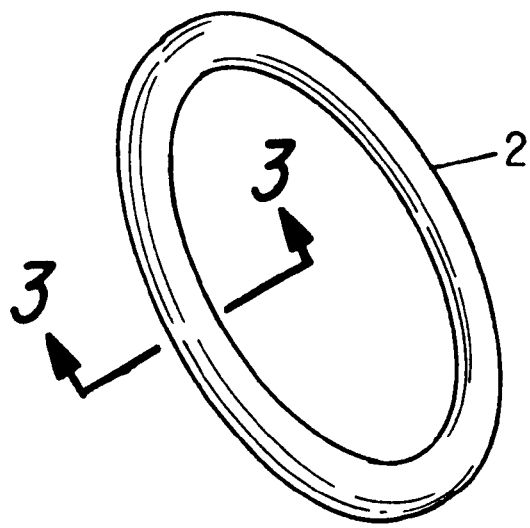
FIG. 2 shows a perspective view of a torroid shaped collar.

The collar 2 is liquid injection molded in conventional fashion in the shape of a torroid or O'ring from a USP class VI medical silicone, reference FIG. 2, with a circular cross-section as shown at FIG. 3. The material is selected to provide a uniform durometer of 40–50 (±5) on the Shore "A" scale over the entire circumference of the collar 2. A variety of other medical grade elastomers and composite materials can also be used alone or in combination, provided they exhibit a desired elasticity and compressive force characteristic. The geometric shape of the collar 2 can also be constructed to be other than a torroid as further discussed below. The collar 2 is post-cured after being removed from an appropriate mold for 4 hours at 400 degrees Fahrenheit. Flashing is removed cryogenically.

The collar 2 can be molded to a number of sizes, for example, having inside diameters of $13/16$, $7/8$, $15/16$, 1 and $1\ 1/16$ inch and cross-section diameters of $1/8$ (±$1/16$) inches. The foregoing sizes will substantially accommodate the penile diameter of men of all races. Only a single size collar, however, is necessary, since the present collar 2 is able to withstand an elongation in excess of 300% per ASTM-D412 standard before breakage occurs and since the collar 2 is designed to exhibit a desired and relatively constant constriction or compression force in the range of 1.5 Kg (±0.5 Kg) over a range of changing collar diameter equal to or greater than 150%.

Also and even though the diameter of the penis typically varies from 50% to 100% from the flaccid to the erect state, the relatively small expansion of the penis in relation to the capabilities of the collar 2 assures that the desired relatively constant constriction force of 1.5 (±0.5 Kg) is obtained for all users.

In normal use and upon fitting the collar 2 to the flaccid penis, within approximately 2 minutes, the user will normally experience an erection. The collar also assists in maintaining an erection if previously achieved. In all cases though the designed compression force characteristic of the collar 2 has been found sufficient to constrict return blood flow and desirably maintain an erection without restricting ejaculation or inducing tissue damage.

Figure 4:
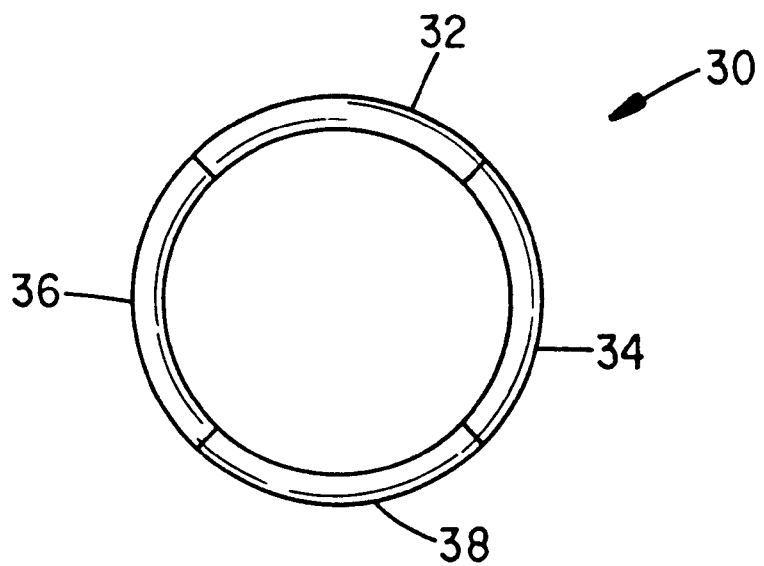
FIG. 4 shows a plan view of a collar molded with multiple zones of different durometer.

Although the collar 2 is presently molded from a uniform mixture of material, FIG. 4 shows a collar 30 that is molded to exhibit multiple circumferential regions 32, 34, 36 and 38 of tailored durometers and/or cross-section shape. The durometer and relative compressive force provided at each of the regions 34–38 can be tailored as desired. In such a fashion, the relative constriction pressure applied to the penile tissues can be controlled to restrict blood flow without discomfort. The number and location of any of available regions can be varied. The color of the material in the different regions 32–38 can also be tailored to facilitate proper placement.

For example and if the region 32 is normally mounted adjacent the urethra, the durometer for the regions 34, 36 and/or 38 can be tailored to be greater than the region 32. Blood flow is thereby constricted without undue constriction or blockage of the urethra.

The cross sectional shapes of the different regions 32–38 can also be tailored as desired to control the magnitude and direction of the applied compressive pressure. For example, alternative cross-section shapes such as shown at FIGS. 5, 6 and 7 can be judiciously molded into the entire collar 2 or selected ones of the regions 32–38 of the collar 30. That is, the region 32 may have one cross-section shape, the regions 34 and 36 another shape and the region 38 still another shape. The regions 34–38 may also each exhibit the same cross section shape.

FIG. 5 shows a collar region having a cross section exhibiting a flat inner surface 40 and hemispherical outer surface 42. FIG. 6 shows a collar region exhibiting an elliptic 44 cross-section shape. FIG. 7 shows a collar region having a cross section exhibiting a flat inner surface 46 and an ellipsoid or ovular outer surface 48.

The cross section shapes of FIGS. 6 and 7 provide additional material that not only affects the durometer magnitude and collar's compressive force, but also varies the directional application of the compressive forces applied to the penis over the length of the corresponding region. That is, the compression force is nominally applied normal to the surface in contact with the penis. The cross section shape can therefore be advantageously varied to control the directional application of the compressive forces to enhance blood occlusion and/or comfort. The outer surface can also include grooves, recesses or protuberances that facilitate gripping and placement of a collar.

The fabrication of collars with selectively tailored regions 32–38 can be achieved in a variety of conventional fabrication processes. For example, multiple injectors can be used at each mold cavity to inject differing materials. Insert molding techniques may also be used, where selected ones of the regions are pre-formed before being cast into a complete collar 30.

The invention has been described with respect to a number of presently preferred constructions and considered improvements and/or alternatives thereto. Still other constructions may be suggested to those skilled in the art. Selected ones of the foregoing features can be used alone and/or can be arranged in different combinations in still other penile constriction collars to achieve the noted desirable effects. The foregoing description should therefore be construed to include all those embodiments within the spirit and scope of the following claims.

What is claimed is:

1. A device for inducing and maintaining a penile erection comprising an endless collar that mounts about a penis, wherein the collar exhibits a continuous circular cross section shape, and wherein the collar is constructed from an elastic material that exhibits a durometer in the range of 40 to 50 (±5) on the Shore "A" scale and defines a substantially constant compressive force through a range of collar expansion equal to or greater than 150%, whereby blood flow is occluded in the penis to enable and sustain an erection without tissue injury.

2. A device as set forth in claim 1 wherein the elastic material exhibits a compressive force in the range of 1.5 Kg (±0.5 Kg) over the range of expansion.

3. A device as set forth in claim 1 wherein said collar exhibits a torroid shape.

4. A device for inducing and maintaining a maintaining penile erection comprising an endless collar that mounts about a penis, wherein the collar exhibits a torroid shape and a continuous circular cross-section, wherein the collar is formed from an elastic material having a durometer in the range of 40–50 (±5) on the Shore "A" scale, and wherein the collar provides a substantially constant compressive force in the range of 1.5 Kg (±0.5 Kg) through a range of collar expansion equal to or greater than 150%, whereby blood flow is occluded in the penis to enable and sustain an erection.

5. A device for inducing and maintaining a penile erection comprising an endless collar that mounts about a penis, wherein said collar includes a plurality of circumferential regions, wherein the collar is formed from at least one elastic material having a durometer in the range of 40–50 (±5) on the Shore "A" scale, and wherein said plurality of regions collectively provide a substantially constant compressive force in the range of 1.5 Kg (±0.5 Kg) over a range of collar expansion equal to or greater than 150%, whereby blood flow is occluded in the penis to enable and sustain an erection.

6. A device as set forth in claim 5 wherein said plurality of regions are formed from elastic materials that exhibit at least two different durometers.

7. A device as set forth in claim 5 wherein said plurality of regions exhibit at least two different cross-section shapes.

8. A device as set forth in claim 5 wherein said plurality of regions collectively exhibit a torroid shape.

9. A device as set forth in claim 5 wherein said plurality of regions are formed from elastic materials that exhibit at least two different durometers and wherein said plurality of regions exhibit at least two different cross-section shapes.

10. A device as set forth in claim 5 wherein one of said plurality of regions exhibits a cross section shape having a flat inner surface and semi-circular outer surface.

11. A device as set forth in claim 5 wherein one of said plurality of regions exhibits an elliptic cross section shape.

12. A device as set forth in claim 5 wherein one of said plurality of regions exhibits a cross section shape having a flat inner surface and an ovular outer surface.

13. A device as set forth in claim 5 wherein said plurality of regions are formed from elastic materials that exhibit at least two different durometers.

14. A method for inducing and maintaining a penile erection comprising the steps of:
 a) selecting an endless elastomer collar having a diameter slightly smaller than the flaccid state of a penis, wherein said collar includes a plurality of regions that extend end-to-end to define the circumference of said collar and wherein first and second regions exhibit different durometers; and
 b) mounting the collar about the base of the penis adjacent the scrotum and aligning said first and second regions to the penis, whereby blood flow is occluded in the penis to enable and sustain an erection without tissue injury.

15. A method as set forth in claim 14 wherein said plurality of regions collectively define a substantially constant compressive force in the range of 1.5 Kg (±0.5 Kg) over a range of collar expansion equal to or greater than 150%.

16. A method as set forth in claim 14 wherein the cross section shape of at least two of said plurality of regions are different.

17. A method as set forth in claim 13 wherein at least one of said plurality of regions exhibits a continuous circular cross section shape.

18. A method as set forth in claim 17 wherein one of the other of said plurality of regions exhibits a cross section shape having a flat inner surface that contacts the penis.

19. A device for inducing and maintaining a penile erection comprising an endless collar that mounts about a penis, wherein the collar exhibits a torroid shape having a continuous circular cross section, and wherein the collar is constructed from an elastic material that defines a substantially constant compressive force in the range of 1.5 Kg (±0.5 Kg) through a range of collar expansion equal to or greater than 150%, whereby blood flow is occluded in the penis to enable and sustain an erection without tissue injury.

20. A device for inducing and maintaining a penile erection comprising an endless collar that mounts about a penis, wherein said collar includes a plurality of circumferential regions, wherein said plurality of regions are formed from elastic materials that exhibit at least two different durometers, and wherein said plurality of regions collectively provide a substantially constant compressive force in the range of 1.5 Kg (±0.5 Kg) over a range of collar expansion equal to or greater than 150%, whereby blood flow is occluded in the penis to enable and sustain an erection.

21. A device for inducing and maintaining a penile erection comprising an endless collar that mounts about a penis, wherein said collar includes a plurality of circumferential regions, wherein one of said plurality of regions exhibits an elliptic cross section shape and wherein said plurality of regions collectively provide a substantially constant compressive force in the range of 1.5 Kg (±0.5 Kg) over a range of collar expansion equal to or greater than 150%, whereby blood flow is occluded in the penis to enable and sustain an erection.

22. A device for inducing and maintaining a penile erection comprising an endless collar that mounts about a penis, wherein said collar includes a plurality of circumferential regions, wherein one of said plurality of regions exhibits a cross section shape having a flat inner surface and an ovular outer surface and wherein said plurality of regions collectively provide a substantially constant compressive force in the range of 1.5 Kg (±0.5 Kg) over a range of collar expansion equal to or greater than 150%, whereby blood flow is occluded in the penis to enable and sustain an erection.

* * * * *